United States Patent [19]
Cadwell

[11] Patent Number: 5,631,667
[45] Date of Patent: May 20, 1997

[54] FREQUENCY AND AMPLITUDE MEASUREMENT TOOL FOR ELECTRONIC DISPLAYS

[75] Inventor: John A. Cadwell, Richland, Wash.

[73] Assignee: Cadwell Industries, Inc., Kennewick, Wash.

[21] Appl. No.: 479,568

[22] Filed: Jun. 7, 1995

Related U.S. Application Data

[63] Continuation of Ser. No. 164,005, Dec. 8, 1993, abandoned.

[51] Int. Cl.$^6$ .................................................. G09G 5/36
[52] U.S. Cl. ............................................ 345/134; 345/157
[58] Field of Search ................................. 345/134, 135, 345/133, 113, 157

[56] References Cited

U.S. PATENT DOCUMENTS

| | | | |
|---|---|---|---|
| 4,053,831 | 10/1977 | Furukawa et al. | 324/77 |
| 4,119,890 | 10/1978 | Kretz | 315/377 |
| 4,237,406 | 12/1980 | Kretz | 315/377 |
| 4,635,050 | 1/1987 | Grothe et al. | 345/113 |
| 4,751,504 | 6/1988 | Slavin | 340/709 |
| 4,754,205 | 6/1988 | Diller et al. | 345/134 |
| 4,761,640 | 8/1988 | Slavin | 340/709 |
| 4,980,763 | 12/1990 | Lia . | |
| 5,004,975 | 4/1991 | Jordan | 324/121 |
| 5,023,783 | 6/1991 | Cohen et al. . | |
| 5,321,420 | 6/1994 | Rezek et al. | 345/134 |

FOREIGN PATENT DOCUMENTS

| | | | |
|---|---|---|---|
| 64123660 | 12/1990 | Japan | 345/134 |

*Primary Examiner*—Richard Hjerpe
*Assistant Examiner*—Regina Liang
*Attorney, Agent, or Firm*—Christensen, O'Connor, Johnson & Kindness PLLC

[57] ABSTRACT

A frequency and amplitude measurement tool for electronic displays is provided. The measurement tool automatically draws a measurement scale (24) on an electronic display screen (12) based upon operator inputs from an input device (18). The operator selects a first point ($x_0, y_0$) by depressing a key (19) on the input device (18), and selects a second point ($x_1, y_1$) by subsequent movement of the input device (18). The measurement tool draws a measurement scale (24) extending between the first and second points. The measurement scale (24) includes horizontal lines and vertical hash lines (54) that subdivide the horizontal distance between the first and second points so that the frequency calculated is an average frequency over the number of cycles represented by the subdivisions. The horizontal lines allow the operator to make amplitude measurements, and the vertical hash lines (54) allow the operator to align the measurement scale (24) with consecutive peaks or valleys of a waveform so that the average frequency of a portion of the waveform can be calculated.

12 Claims, 4 Drawing Sheets

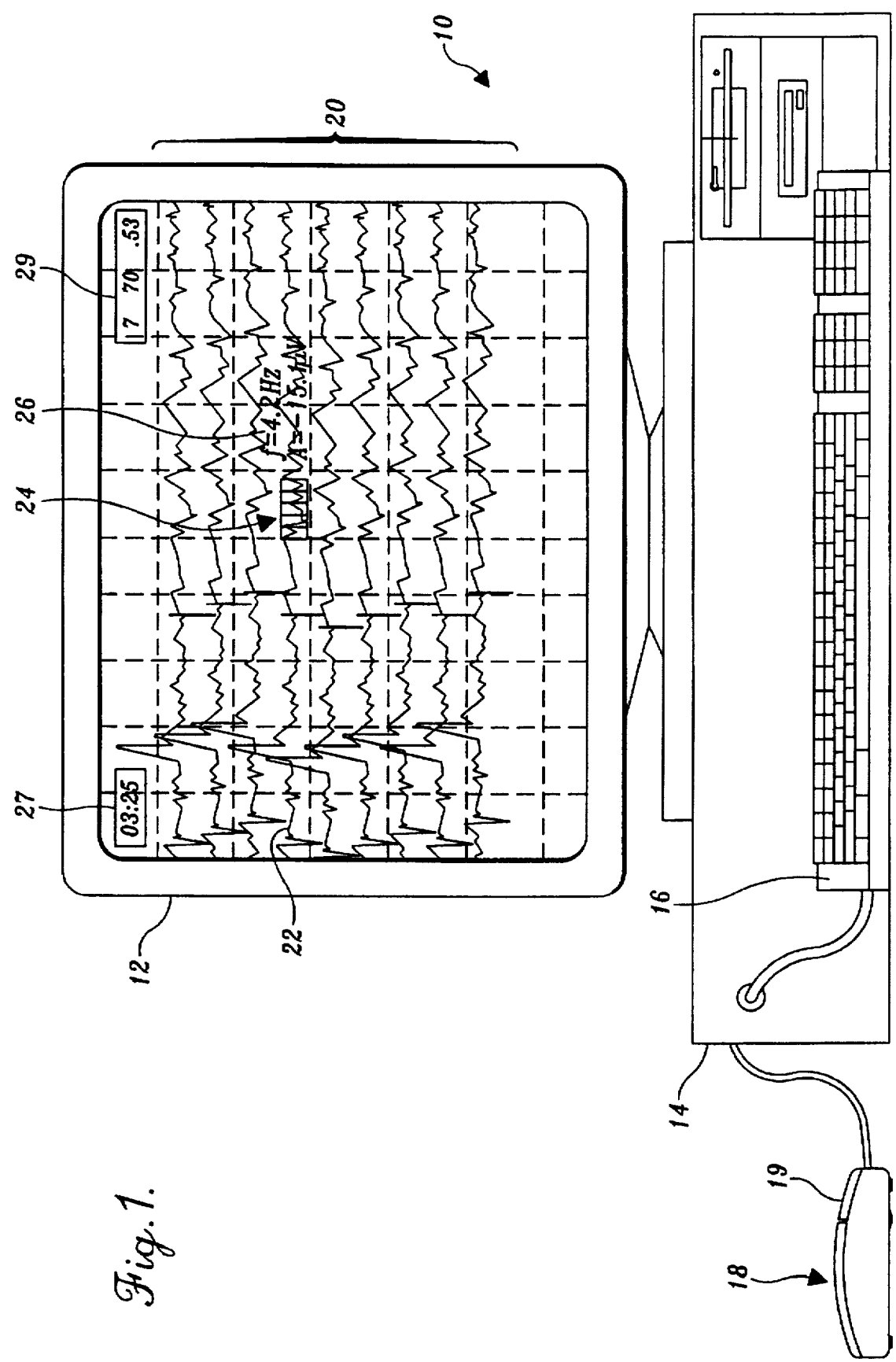

FREQUENCY AND AMPLITUDE MEASUREMENT TOOL FOR ELECTRONIC DISPLAYS

This application is a continuation application based on prior application Ser. No. 08/164,005, filed on Dec. 8, 1993 now abandoned.

FIELD OF THE INVENTION

This invention relates generally to waveform measurement tools and, more particularly, to an electronic measurement tool for measuring a representative amplitude and an average frequency of an EEG waveform displayed on an electronic display screen.

BACKGROUND OF THE INVENTION

The primary medical instrument used to monitor the electrical activity of a patient's brain is the electroencephalograph (EEG). EEGs monitor brain activity by measuring the very small voltage fluctuations that are generated in the brain, which are detected by electrodes attached to a patient's scalp. To aid in studying these analog signals, a record of the voltage fluctuations (called an electroencephalogram) is often made over time. Traditionally, electroencephalograms are made using a mechanical EEG recorder that employs pens to record the analog voltage fluctuations on a strip of paper. As a continuous chart of paper is moved beneath an array of galvanometer-driven ink pens, the pens trace out the brain wave activity as a series of wavy or jagged lines.

Medical personnel analyze EEG waveforms (electroencephalograms) representing neural activity at various points on a patient's brain when monitoring, diagnosing, and treating the patient. Of particular importance to medical personnel are dominant frequency components, e.g., the modal frequency, of portions of the EEG waveforms. Medical personnel typically need to know the average frequency and a representative amplitude of the dominant frequency components of the various EEG waveforms. This frequency and amplitude information allows, for example, medical personnel to compare neural activity at various points on the patient's brain. With traditional paper EEG recorders, medical personnel measure frequencies and amplitudes using a transparent plastic ruler that has several frequency scales printed on it. The ruler is superimposed over the waveforms on the paper, the closest matching frequency scale is aligned with the waveform, and the frequency is that printed on the ruler. The ruler may have another scale for measuring the distance between a peak and valley of the waveform so as to determine a representative amplitude. Similar measurements can be taken on various waveforms for making comparisons. For the ruler to provide valid measurements, the frequency scales printed on the ruler must be calibrated for a particular paper speed (e.g., 30 mm/sec.) of the EEG recorder, and the amplitude scale must be calibrated the same as the vertical displacement calibration of the EEG recorder (e.g., 7 μvolt/mm).

Recently, work has begun on digital EEG recorders to replace analog EEGs and their associated mechanical pen-on-paper recorders. Instead of printing the EEG waveforms on paper, digital EEG recorders convert sensed analog waveforms into digital signals that are stored in some digital storage medium such as random access memory (RAM), hard disks, storage tapes, etc. The stored digital waveforms can then be transferred to a digital EEG reader for display and analysis by medical personnel. A digital EEG reader can consist of a stock personal computer including memory, a processor, input devices and an electronic display screen, e.g., a cathode ray tube (CRT) monitor, for displaying the waveforms. On such display screens, a transparent plastic ruler as used in the past with paper EEG recorders can conceivably be used to measure frequency and amplitude. Unfortunately, however, if the display screen size is changed or if a different display calibration is used, the same plastic ruler will no longer be properly calibrated. Furthermore, the use of a plastic ruler on a display screen can be cumbersome.

With the introduction of digital EEG recorders and readers, an easier and more flexible approach is desirable and feasible. In fact, presently there are electronic systems that provide waveform frequency and amplitude measurements. However, the measurements provided by presently available systems are not well suited for EEG measurements. Most systems perform complex mathematical analyses (i.e., Fourier transforms) that give the entire frequency spectrum of the EEG waveform. In other words, such mathematical analyses give the amplitudes and frequencies of a band of frequencies that form an EEG waveform. The majority of this information is not useful and, many times, not accurate as the most significant frequencies tend to be spread out over a band of frequencies.

Rather than all this complex information, what is most significant is the average frequency and a representative amplitude of a dominant frequency component (e.g., the modal frequency). Medical personnel can visually pick out significant frequency components. A simple and flexible tool that allows medical personnel to measure a representative amplitude and the average frequency of visually selected frequency components is needed. While method and apparatus do currently exist for electronically measuring the frequency of a selected frequency component, the measurements can only be based on a single cycle of the frequency component. This makes the measurements very sensitive to operator error and minor fluctuations in waveforms.

The present invention is directed to overcoming the foregoing problems by providing a method and apparatus that allows medical personnel to electronically measure the average frequency and a representative amplitude of a desired frequency component of an EEG waveform using conventional computer input devices. The method and apparatus is self calibrating. As a result, the same tool can be used to easily measure frequencies and amplitudes on various monitor sizes using various display calibrations.

SUMMARY OF THE INVENTION

In accordance with this invention, a method and apparatus for measuring the average frequency and a representative amplitude of a selected frequency component of an EEG waveform is provided. The invention is primarily intended to be used with digital EEG recorders and readers. Such new recorders store EEG waveforms digitally for display on a digital EEG reader formed, for example, by a personal computer that includes an electronic display screen, a processor, memory, and input devices such as a keyboard and mouse. The invention is integrated into a digital EEG reader to allow an operator to electronically overlay a measurement scale on the reader display screen for making frequency and amplitude measurements of displayed EEG waveforms. Using an input device such as a mouse, the operator selects a first point on the waveform by locating a cursor at the first point and pressing a mouse key. A processor programmed in accordance with the invention responds by recording the point selected by the operator.

Then, as the operator moves the mouse, the processor forms a measurement scale that expands and contracts in accordance with the movement of the mouse, that is, the measurement scale extends from the first point selected to a second point selected by movement of the mouse.

The processor subdivides the measurement scale into a plurality of equal increments (e.g., 5) and displays these subdivisions on the display screen by drawing vertical hash lines. As the operator moves the mouse, the scale along with the vertical hash lines are repetitively redrawn based on the new location of the second point. This repetitive redrawing allows the operator to "stretch and shrink" the scale until the vertical hash lines align with consecutive peaks or valleys of a displayed waveform. Each time the processor redraws the measurement scale, an average frequency is calculated based upon the number of subdivisions, a horizontal calibration factor, and the horizontal distance between the first point originally selected and the present screen position dictated by movement of the mouse. For example, the horizontal distance can be multiplied by the horizontal calibration factor to determine the time period represented by the portion of the waveform overlaid by the measurement scale. The elapsed time can then be inverted to obtain a frequency that would then be scaled by the number of scale subdivisions to obtain the frequency represented by the subdivisions.

In accordance with further aspects of the present invention, an operator can take representative measurements of the amplitude of an EEG waveform. The processor repetitively monitors the vertical distance between the first point selected on the screen and the present point dictated by movement of the mouse. The vertical distance is then multiplied by an appropriate vertical calibration factor to determine the amplitude in appropriate units, e.g., microvolts. The processor displays the amplitude and frequency calculated each repetition on the display screen adjacent to the measurement scale.

In one preferred embodiment of the invention, the measurement scale is drawn as a rectangular frame with vertical hash lines subdividing the frame into multiple subdivisions. The user defines one corner of the rectangular frame by selecting a first screen position with the mouse. The diagonally opposite corner of the rectangular frame is defined by a second screen position selected with the mouse. As the mouse is moved, the measurement scale is repetitively erased and redrawn to track the new second screen position selected by the operator moving the mouse. The distance between the top and bottom sides of the rectangular frame, which the operator aligns, is the basis for the amplitude measurement, and the distance between adjacent vertical hash lines is the basis for the frequency measurement.

As will be appreciated from the foregoing brief summary, the method and apparatus formed in accordance with the invention provides a flexible system for electronically determining average frequencies and representative amplitudes of selected portions of a waveform, such as an EEG waveform. The system can be used with various display screen sizes and various display calibrations without the operator having to make any adjustments. The system forms an average frequency by drawing a subdivided measurement scale that the operator aligns with a series of peaks or valleys of the waveform. Because the average frequency is based on several cycles of a waveform, the frequency measurement is not sensitive to minor operator error or fluctuation in waveforms. The operator is able to make amplitude measurements by aligning upper and lower horizontal lines of the measurement scale with peaks and valleys of the waveform.

Accordingly, the operator is able to easily and accurately measure the average frequency and a representative amplitude of a selected waveform portion without the use of traditional plastic rulers. Furthermore, the measurements are based on simple calculations so that the operator is in full control of the measurements, that is, the measurements are not based on complex mathematics that an operator can not directly control or monitor.

BRIEF DESCRIPTION OF THE DRAWINGS

The foregoing features and advantages will be better understood from the following description of preferred embodiments of the present invention when taken in conjunction with the accompanying drawings, wherein:

FIG. 1 illustrates a digital EEG reader system with which the present invention is ideally used;

DETAILED DESCRIPTION OF THE PREFERRED EMBODIMENT

Figure 2A:
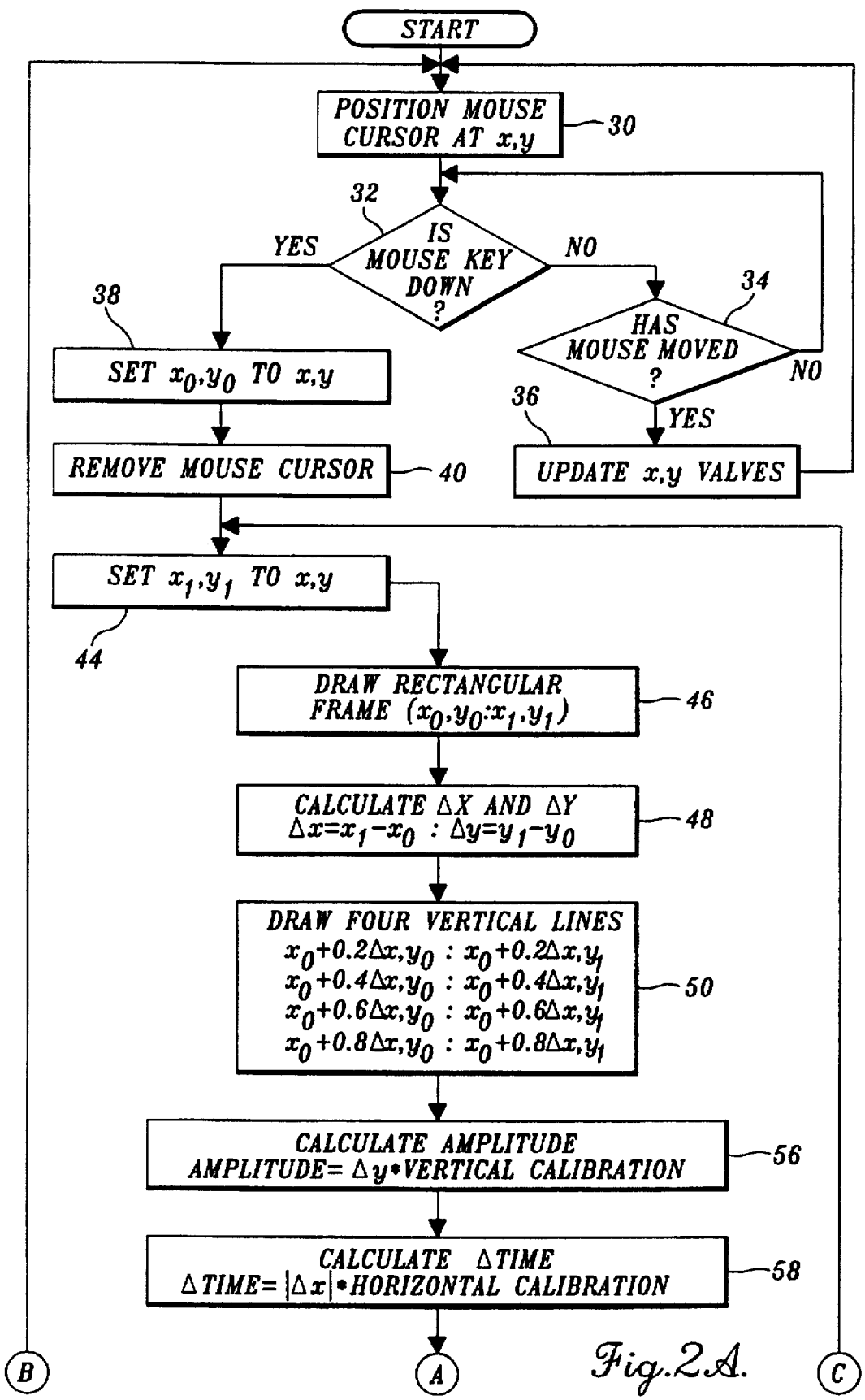
FIGS. 2A and 2B show a flow diagram illustrating the method of operation of the present invention.

FIG. 1 is a pictorial illustration of apparatus that can be used to form a digital EEG reader station 10 in which the present invention can be implemented. In the preferred embodiment, the digital EEG reader 10 receives digital signals representing EEG waveforms from a digital EEG recorder (not shown). When taking EEG measurements, sensors are attached at various points on a patient's head. Analog signals produced by the sensors are transmitted to the digital EEG recorder. The EEG recorder converts the analog signals into corresponding digital signals, which are transmitted to the EEG reader 10 for displaying the EEG waveforms so that they can be analyzed by medical personnel. The EEG waveforms can be displayed upon receipt from the EEG recorder or, alternatively, the EEG waveforms can be stored on a suitable medium, such as an optical disk, and later displayed on the EEG reader.

The digital EEG reader 10 can be formed using presently available personal computers. The reader 10 includes an electronic display screen 12 (e.g., a cathode ray tube (CRT) display monitor); a keyboard 16; a mouse 18; and a processor module 14 including a central processing unit (CPU), memory, and storage devices such as disks and tapes. The processor module 14 stores and processes the digital data produced by the digital EEG recorder so that the waveforms 20 represented by the data are displayed on the display screen 12. Horizontal distance on the display screen 12 represents time, and vertical distance represents voltage, so that a given waveform, such as the waveform 22, represents the voltage at a particular sensor location over time.

The invention allows an operator to measure frequencies and amplitudes of the waveforms 20 through the use of an input device such as the mouse 18. When the processor module 14 is programmed in accordance with the invention, an operator can use the mouse 18 to determine the average frequency and a representative amplitude of, for example, a portion of the waveform 22. Using the mouse 18, the operator positions a measurement scale 24 and then stretches and shrinks the scale 24 horizontally so that vertical hash lines in the scale 24 align with consecutive peaks or valleys of the waveform 22. Based upon the distance between the vertical hash lines, the average frequency is calculated and displayed at a position 26 near the scale 24. The operator is also able to stretch and shrink the scale 24 vertically so as to position upper and lower horizontal lines of the scale 24 at peaks and valleys of the waveform 22. Based upon the distance between the upper and lower horizontal lines, the amplitude is calculated and displayed at the position 26 near the scale 24.

The operator is able to select which frequency component of the waveform 22 to analyze by choosing with which peaks or valleys to align the vertical hash lines of the scale 24. The operator would typically choose to analyze a dominant frequency, e.g., the modal frequency. The processor module 14 automatically calibrates the scale 24 based upon the size of the display screen 12 and the display scale of the waveforms 20, so that the operator makes frequency and amplitude measurements using the same tool and technique, namely, positioning of the scale 24 with the mouse 18. The digital EEG reader 10 may be programmed to display additional data on the display screen 12. For example, record time 27 and amplifier settings 29 including amplitude and paper speed settings can be displayed as shown in FIG. 1.

Figure 2B:
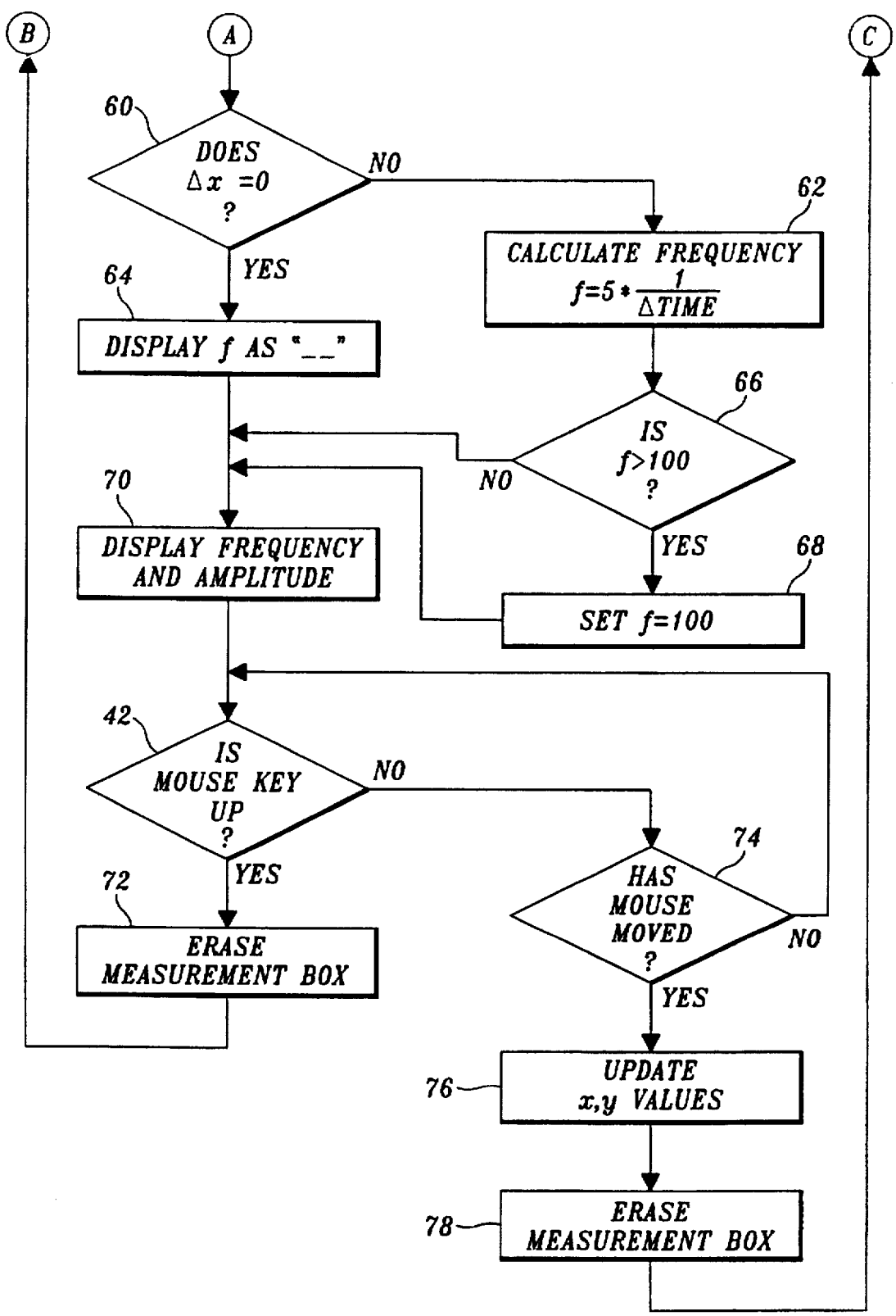

FIGS. 2A and 2B are flow diagrams illustrating one preferred method of operation of the invention. That is, the CPU of the processor module 14 is preferably programmed to perform the steps shown in FIGS. 2A and 2B. The rectangular boxes shown in FIGS. 2A and 2B represent steps that the CPU performs, and the diamonds represent decision steps performed by the CPU to determine which subsequent steps to perform.

Figure 3:
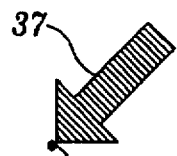
FIG. 3 illustrates a display cursor used in one preferred embodiment of the invention.

The method begins with the steps indicated by the boxes 30 through 36. These steps control the position of a cursor on the display screen 12 so that the cursor's position responds to movement of the mouse 18. Various shapes can be used for the cursor, such as the arrow 37 illustrated in FIG. 3. Movement of the mouse 18 causes corresponding movement of the mouse cursor 37 on the display screen 12. As indicated by the box 30, initially the mouse cursor 37 is positioned at coordinates x,y, where x is horizontal distance and y is vertical distance on the display screen 12 relative to some selected reference point. At system startup, the coordinates x,y are initialized at some chosen initialization values, for example, values that would position the mouse cursor initially at the center of the display screen 12.

After positioning the mouse cursor 37 at the coordinates x,y, the step enclosed in the decision diamond 32 is executed to determine whether the mouse cursor 37 will continue to be displayed. Until a mouse key 19 is depressed, the mouse cursor continues to be displayed and follows movement of the mouse 18. In particular, if the step at decision diamond 32 determines that the mouse key 19 has not been depressed, a determination is made at the decision diamond 34 as to whether the mouse has been moved. If the mouse has not been moved, the cursor is not modified and program control loops back to the decision diamond 32 to determine whether the mouse key 19 has been depressed. On the other hand, if the mouse has been moved, the coordinates x,y are updated based on the movement of the mouse, as indicated at the box 36, and then program control loops back to the step at box 30 to reposition the mouse at the updated coordinates x,y.

When a determination is made at the decision diamond 32 that the mouse key 19 is being depressed, a starting point $x_0,y_0$ of the measurement scale 24 is set to the present position x,y of the cursor, as expressed in the box 38, and as indicated at the box 40, the mouse cursor is then erased from the display screen. Thereafter, the remaining steps shown in FIGS. 2A and 2B repetitively redraw the measurement scale 24 to extend between the starting point $x_0,y_0$ and a second point $x_1,y_1$ controlled by subsequent movement of the mouse. The measurement scale 24 is repetitively redrawn to extend to new positions of the second point $x_1,y_1$ dictated by mouse movement, until, as indicated by the decision diamond 42 in FIG. 2B, the mouse key 19 is released. In each repetition of redrawing the measurement scale 24, a frequency and amplitude are calculated based upon the size of the measurement scale 24.

Figure 4A:
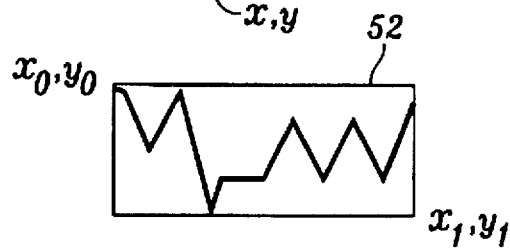
FIGS. 4A, 4B, and 4C illustrate how a measurement scale is progressively drawn and the average frequency and a representative amplitude displayed in accordance with the method shown in FIGS. 2A and 2B.
Figure 4B:
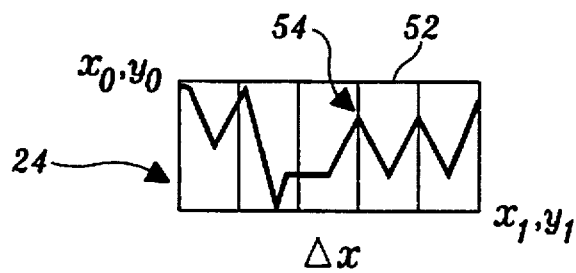
Figure 4C:
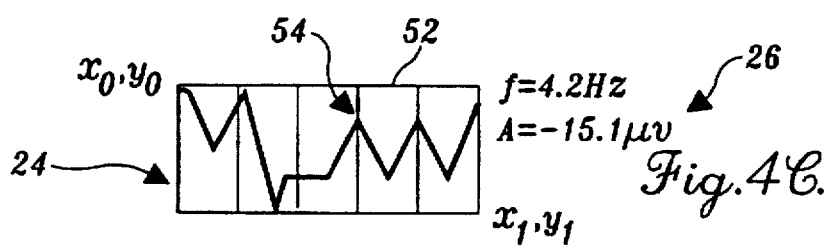

The steps for drawing the measurement scale 24 are indicated by the boxes 44, 46, 48 and 50, and the corresponding progressive shape of the measurement scale 24 in one preferred embodiment is illustrated in FIGS. 4A, 4B and 4C. First, as indicated at the box 44, the second point $x_1,y_1$ is set to the current display screen location stored in the coordinates x,y, which are dictated by movement of the mouse. Together the first point $x_0,y_0$ and the second point $x_1,y_1$ define the measurement scale 24 so that the first coordinates $x_0,y_0$ are one corner of a rectangular frame 52 and the second coordinates $x_1,y_1$ are the diagonally opposite corner of the rectangular frame 52, as shown in FIG. 4A. The step indicated at box 46 causes the rectangular frame shown in FIG. 4A to be drawn. Next, the step indicated at box 48 calculates the length $\Delta x$ and height $\Delta y$ of the rectangular frame 52 by respectively determining the difference between the second and first x-coordinates and the second and first y-coordinates. The step indicated at box 50 is then executed to subdivide the length of the rectangular frame 52. In the preferred embodiment shown in FIG. 4B, the rectangular frame is subdivided into five equal sections by drawing four equally-spaced vertical hash lines 54 between the sides of the frame 52. The x-coordinates of the hash lines 54 are calculated by adding fractions (i.e., 0.2, 0.4, 0.6, and 0.8) of the frame length $\Delta x$ to the first x-coordinate $x_0$. The y-coordinates of the hash lines 54 are the y-coordinates of the first and second points (i.e., $y_0$ and $y_1$) so that the hash lines extend from the bottom to the top of the rectangular frame 52.

After drawing the rectangular frame 52 along with the hash lines 54, a frequency and amplitude are calculated and displayed as indicated by the steps shown in boxes 56 through 70. At the step indicated by box 56, the amplitude A is calculated by multiplying the height $\Delta y$ of the rectangular frame 52 by a vertical calibration factor stored in memory. The vertical calibration factor converts the vertical distance on the display screen 12 into appropriate measurement units, e.g., microvolts for EEG measurements. Similarly, the length $\Delta x$ of the rectangular frame 52 is converted into a time period $\Delta TIME$ as indicated by the box 58. In particular, the absolute value of the length $\Delta x$ is multiplied by a horizontal calibration factor that is stored in memory and corresponds to the horizontal scale of the display screen 12. By pre-storing various vertical and horizontal calibration factors to correspond to various display scales, an operator can make frequency and amplitude measurements without having to select different rulers as is required in traditional paper EEG recorders.

The frequency is calculated based upon the time period $\Delta TIME$ unless the width of the frame 52 is zero or so small that the corresponding frequency is above frequencies of interest, all as indicated by the steps in boxes 60 through 68. First, at the decision diamond 60, a determination is made as to whether the rectangular frame 52 has any width, i.e., whether the horizontal displacement $\Delta x$ is zero. If the rectangular frame 52 has no width, the operator has not yet "stretched" out the measurement scale 24 to make a frequency measurement. In this case, as indicated by the step at box 64, the frequency is displayed as a null value, such as a short underscore line, displayed at the position 26 where the frequency and amplitude are normally displayed in accordance with the step indicated by box 70.

If, on the other hand, the rectangular frame 52 has a non-zero width, the frequency is calculated at the step indicated at the box 62 by inverting the time period $\Delta$TIME and multiplying the resulting value by a factor of five to account for the five subdivisions of the rectangular frame 52. If the width of the rectangular frame 52 is so narrow that the calculated frequency is greater than 100, the frequency is set to 100 Hz, as indicated by the decision diamond 66 and the box 68. In EEG applications of the invention, the frequency is preferably limited to a maximum value in this manner as higher frequencies are typically not of interest. If, at the decision diamond 66, a determination is made that the frequency is not greater than 100, the frequency value calculated at the step at box 62 is not modified. Either way, program control then flows to the step indicated by the box 70 at which the calculated frequency and amplitude are displayed at the position 26, as shown in FIGS. 1 and 4C.

The remaining steps indicated by the decision diamond 42 and the boxes 72 through 78 update the measurement scale 24, depending upon whether the mouse key 19 has been released or the mouse has been moved with the mouse key 19 still depressed. If a determination is made at the decision diamond 42 that the mouse key 19 has been released, the measurement scale 24 is erased as indicated by the step at box 72. After erasing the measurement scale 24, program control loops back to the start of the flow diagram in FIG. 2A to the step at box 30 that causes the mouse cursor to be redrawn at the presently selected point x,y, so that the operator can position and draw a new measurement scale 24.

If, on the other hand, the mouse key 19 is still depressed, the measurement scale 24 is not erased and a determination is made at the decision diamond 74 as to whether the mouse has been moved. If the mouse has not been moved, program control loops back to the decision diamond 42, where a determination is again made as to whether the mouse key 19 has been released. If, however, it is determined at decision diamond 74 that the mouse has been moved, the coordinates x,y representing the presently selected screen position are updated based upon the mouse movement, as indicated at the box 76. After updating the present coordinates x,y, the measurement scale 24 is erased as indicated by the step at box 78, and program control loops back to the step at box 44 where the second point $x_1,y_1$ defining one corner of the measurement scale 24 is set to the coordinates x,y. The measurement scale is then redrawn and amplitude and frequency recalculated by the same steps previously described.

Figure 5A:
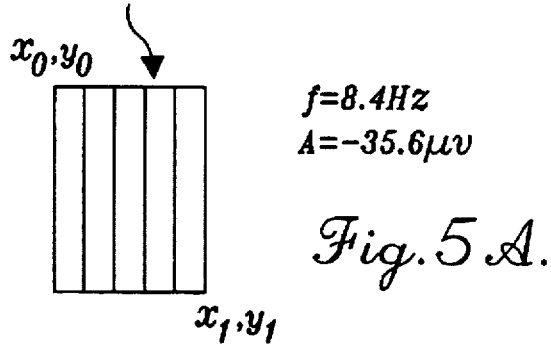
FIGS. 5A 5B, and 5C illustrate how the measurement scale and corresponding frequency and amplitude change as the scale is "stretched and shrunk" by movement of an operator input device, such as the mouse shown in FIG. 1.
Figure 5B:
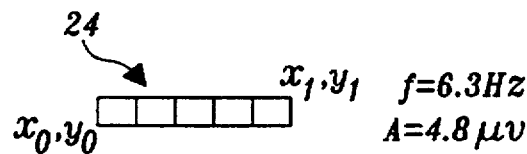

It will be appreciated that the just described method allows an operator to control frequency and amplitude measurements by positioning and sizing the measurement scale 24. The length of the measurement scale 24 created by operator movement of the mouse controls the frequency measurement, and the height of the measurement scale 24 determines the amplitude. The operator positions a first point $x_0,y_0$ and then stretches and shrinks the measurement scale 24 horizontally from this first point $x_0,y_0$ to a second point $x_1,y_1$ to align the vertical hash lines 54 with consecutive peaks or valleys of a selected portion of a waveform to measure average frequency. To measure an amplitude, the operator stretches and shrinks the measurement scale vertically from the first point $x_0,y_0$ to a second point $x_1,y_1$ to align the top and bottom sides of the measurement scale 24 with a portion of the waveform. For example, if the measurement scale shown in FIG. 4C is shrunk horizontally and stretched vertically by movement of the mouse while depressing the mouse key 19, the measurement scale 24 changes shape to that shown in FIG. 5A. Shrinking the box horizontally causes the frequency to increase, and stretching the box vertically causes the amplitude to increase in magnitude. In contrast, if the box is stretched horizontally and shrunk vertically, the frequency and amplitude both decrease in the magnitude, as shown in FIG. 5B.

Figure 5C:
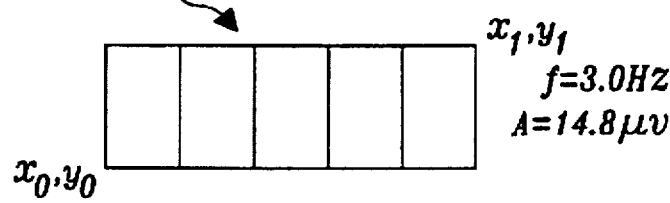

In one preferred embodiment, downward amplitude measurements are negative and upward amplitude measurements are positive. That is, as shown in FIGS. 4C and 5A, when the measurement scale is stretched downward from the first point $x_0,y_0$ the amplitude is displayed as a negative value, and when the box is stretched upward, as shown in FIGS. 5B and 5C, the amplitude is displayed as a positive value. These amplitude signs result if the mathematical calculations indicated at the steps in blocks 48 and 56 of FIG. 2A are used with the vertical calibration factor set to a positive value. In contrast, in the preferred embodiment the frequency measurements are always positive, i.e., whether the measurement scale is extended to the right or left. This is accomplished by the step at block 58 where the absolute value of the horizontal distance $\Delta x$ is used in conjunction with a positive horizontal calibration factor to calculate frequency. In other embodiments of the invention, it may be more desirable to also have only positive amplitudes, which can be similarly accomplished by using the absolute value of the vertical distance $\Delta y$ along with a positive vertical calibration factor at the step in block 56.

Figure 6:
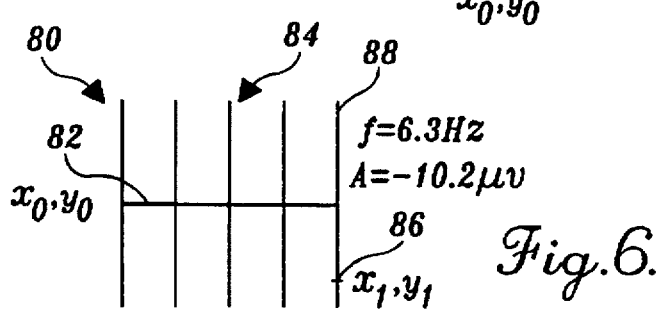
FIG. 6 shows a measurement scale drawn in accordance with an alternative embodiment of the invention.

The measurement scale 24 shown in FIGS. 4C, 5A, 5B, and 5C illustrates one preferred shape for the measurement scale. However, it will be readily appreciated that other geometric shapes can be used to provide a measurement scale. FIG. 6 illustrates one alternative shape. The measurement scale 80 shown in FIG. 6 consists of a horizontal line 82 extending from the first point $x_0,y_0$ horizontally to a second point $x_1,y_0$, where the second x-coordinate $x_1$ is defined by operator movement of the mouse after selecting the first point $x_0,y_0$. The measurement scale 80 also includes vertical hash lines 84 at the ends of the horizontal line 82 and at equally spaced intermediate points along the horizontal line 82. The measuring scale shown in FIG. 6 has five vertical hash lines 84 so that four subdivisions are created and frequency measurements represent an average over four cycles. However, more or less vertical hash lines 84 could be used to create some other number of subdivisions. The vertical hash lines 84 extend a predefined vertical distance that preferably does not vary with operator movement of the mouse and is sufficient to encompass the range of amplitudes of interest. A horizontal hash mark 86 at the second point $x_1,y_1$, defined by operator movement of the mouse, allows the operator to align the measurement scale 80 with points on a waveform so that amplitude measurements can be made. In particular, the horizontal hash mark 86 extends up and down along the vertical hash line 88 as the mouse is moved up and down. The amplitude measurement is based on the vertical distance between the first point $x_0,y_0$ and the second point $x_1,y_1$ represented by the hash mark 86. One advantage of having fixed-height vertical hash lines 84 along with the sliding hash mark 86 is that the operator is able to see the subdivisions of the measurement scale, so that the measurement scale can be aligned with a waveform regardless of how the mouse is moved vertically.

While the preferred embodiment of the invention has been illustrated and described, it will be appreciated that various changes, in addition to those previously mentioned herein, can be made therein without departing from the spirit and scope of the invention. For example, while the measurement scale 24 is shown in FIGS. 4C, 5A, 5B and 5C with five subdivisions so that the frequency represents an average frequency over five cycles, the number of subdivisions can be increased or decreased, e.g., four or six subdivisions could be used. Furthermore, while in the preferred embodiment described the measurement scale 24 is stretched and shrunk by movement of the mouse with the mouse key 19 depressed, this logic could be easily changed. For example, the first point $x_0,y_0$ of the measurement scale 24 could be selected by clicking (i.e., depressing and releasing) the mouse key 19. Then with the mouse key released, movement of the mouse could be used to expand and contract the measurement scale to a second point $x_1,y_1$. A subsequent clicking of the mouse key 19 could be used to erase the measurement scale 24 so that the measurement scale could be repositioned. Thus, within the scope of the appended claims, it is to be understood that the invention can be practiced otherwise than as specifically described herein.

The embodiments of the invention in which an exclusive property or privilege is claimed are defined as follows:

1. A frequency measurement tool for measuring the average frequency of several cycles of a plurality of cycles of a variable-frequency, multiple-cycle waveform displayed on an electronic display, said frequency measurement tool including:
    (a) an electronic display displaying a plurality of cycles of a variable-frequency, multiple-cycle waveform;
    (b) an input device for allowing an operator to select two points on said display located at opposite ends of several cycles of said plurality of cycles of said variable-frequency, multiple-cycle waveform displayed on said electronic display; and
    (c) a data processor, coupled to said input device and said electronic display, for:
        (i) subdividing the horizontal distance between said two points into a plurality of equi-spaced apart subdivisions,
        (ii) drawing a measurement scale over said several cycles of said plurality of cycles between said two points, said measurement scale including a plurality of vertical hash lines that overlie said several cycles of said plurality of cycles and subdivide said horizontal distance between said points into said plurality of equi-spaced apart subdivisions,
        (iii) calculating a frequency based upon the number of said plurality of equi-spaced apart subdivisions and said horizontal distance between said two points, and
        (iv) displaying said calculated frequency on said electronic display.

2. The frequency measurement tool of claim 1, wherein said input device is responsive to manipulation by the operator so that the operator can modify the position of the second point of said two points, said data processor monitoring said manipulation of said input device so that, when said manipulation of said input device occurs, said data processor causes said measurement scale to be erased and then redrawn to extend between the first point of said two points and said second point as modified by said manipulation of said input device, so that the operator is able to align said plurality of vertical hash lines with consecutive peaks or valleys of said several cycles of said plurality of cycles, so that, when said plurality of vertical hash lines is aligned with said consecutive peaks or valleys of said several cycles of said plurality of cycles, said frequency is representative of the average frequency of said several cycles of said plurality of cycles.

3. The frequency measurement tool of claim 1, wherein said plurality of vertical hash lines are aligned horizontally and include first and second vertical hash lines respectively intersecting the first and second points of said two points, said plurality of vertical hash lines further including a predetermined number of additional vertical hash lines lying between said first and second vertical hash lines.

4. The frequency measurement tool of claim 1, wherein said frequency measurement tool also provides an amplitude measurement based upon the vertical distance between said two points, so that the operator is able to make amplitude measurements by selecting positions for said two points on said electronic display.

5. The frequency measurement tool of claim 4, wherein:
    said measurement scale also includes first and second horizontal lines, said first and second horizontal lines and first and second ones of said plurality of vertical hash lines together forming a rectangular frame;
    said first point lies at one corner of said rectangular frame and said second point lies at the diagonally opposite corner of said rectangular frame; and
    other ones of said plurality of vertical hash lines extend between said first and second horizontal lines.

6. The frequency measurement tool of claim 4, wherein the waveforms displayed on said electronic display are electroencephalograms and wherein said frequency measurement tool is used to analyze at least one electroencephalogram displayed on said electronic display.

7. A method of providing operator-controlled frequency measurements of the average frequency of several cycles of a plurality of cycles of a variable-frequency, multiple-cycle waveform displayed on an electronic display, said method comprising:
    (a) selecting two points located at opposite ends of several cycles of a plurality of cycles of a variable-frequency, multiple-cycle waveform displayed on an electronic display;
    (b) subdividing the horizontal distance between said two points into a plurality of equi-spaced apart subdivisions;
    (c) drawing a measurement scale over said several cycles of said plurality of cycles of said variable-frequency, multiple-cycle waveform displayed on said electronic display between said two points, said measurement scale including a plurality of vertical hash lines that overlie said several cycles of said plurality of cycles and subdivide the horizontal distance between said two points into said plurality of equi-spaced apart subdivisions;
    (d) calculating a frequency based on said horizontal distance between said two points and the number of said plurality of equi-spaced apart subdivisions; and
    (e) displaying said calculated frequency on said electronic display.

8. The method claimed in claim 7, further including
    monitoring for an indication of the operator's desire to modify the position of the second point of said two points; and when receiving said indication, erasing said measurement scale and then redrawing said measurement scale to extend between the first point of said two points and said second point modified in accordance with said indication, so that the operator is able to align said plurality of vertical hash lines with the consecutive peaks or valleys of said several cycles of said plurality of cycles of said variable-frequency, multiple-cycle waveform displayed on said electronic display, so that when said plurality of vertical hash lines is aligned with said consecutive peaks or valleys of said several cycles of said plurality of cycles said calculated frequency is representative of the average frequency of said several cycles of said plurality of cycles of said variable-frequency, multiple-cycle waveform displayed on said electronic display.

9. The method claimed in claim 11, wherein said plurality of vertical hash lines are aligned horizontally and include first and second vertical hash lines respectively intersecting the first and second points of said two points, said plurality of vertical hash lines further including other vertical hash lines lying between said first and second vertical hash lines.

10. The method claimed in claim 12, wherein said method also includes allowing the operator to make amplitude measurements by;

(a) calculating an amplitude based upon the vertical distance between said two points; and (b) displaying said amplitude on said electronic display.

11. The method claimed in claim 10, wherein:

said measurement scale includes first and second horizontal lines;

said first and second horizontal lines and first and second ones of said plurality of vertical hash lines together forming a rectangular frame;

said first point lies at one corner of said rectangular frame and said second point lies at the diagonally opposite corner of said rectangular frame; and other ones of said plurality of vertical hash lines extend between said first and second horizontal lines.

12. The method claimed in claim 10, wherein the waveforms displayed on said electronic display are electroencephalogram and wherein said method is used to analyze at least one electroencephalogram displayed on said electronic display.

* * * * *

UNITED STATES PATENT AND TRADEMARK OFFICE
CERTIFICATE OF CORRECTION

PATENT NO. : 5,631,667
DATED      : May 20, 1997
INVENTOR(S) : J.A. Cadwell

It is certified that error appears in the above-indentified patent and that said Letters Patent is hereby corrected as shown below:

| COLUMN | LINE | | |
|---|---|---|---|
| 10 (Claim 8, | 64 line 1) | After "including" insert --:-- | |
| 11 (Claim 9, | 17 line 1) | "claim 11," should read --claim 7,-- | |
| 11 (Claim 10, | 23 line 1) | "claim 12," should read --claim 7,-- | |
| 11 (Claim 10, | 25 line 3) | After "by" delete ";" and insert --:-- | |
| 12 (Claim 12, | 20-21 lines 2-3) | "electroencephalogram" should read --electroencephalograms-- | |

Signed and Sealed this

Ninth Day of September, 1997

Attest:

BRUCE LEHMAN

Attesting Officer

Commissioner of Patents and Trademarks